United States Patent [19]

Cardarelli et al.

[11] Patent Number: 4,634,693

[45] Date of Patent: Jan. 6, 1987

[54] TIN STEROIDS AND THEIR USES

[76] Inventors: Nathan F. Cardarelli, 439 Crestwood Ave., Akron, Ohio 44302; Sebastian V. Kanakkanatt, 2459 Audubon Rd., Akron, Ohio 44320

[21] Appl. No.: 764,650

[22] Filed: Aug. 12, 1985

Related U.S. Application Data

[63] Continuation-in-part of Ser. No. 518,073, Jul. 28, 1983, Pat. No. 4,541,956.

[51] Int. Cl.⁴ .......................... C07J 1/00; A01N 45/00
[52] U.S. Cl. .................................... 514/169; 514/178; 514/182; 260/397.4; 260/397.1; 260/397.2; 260/397.3; 260/397.47
[58] Field of Search ...................... 514/178, 182, 169; 260/397.4, 397.1

[56] References Cited

U.S. PATENT DOCUMENTS 4,541,956  9/1985  Cardarelli et al. ............... 260/397.1

Primary Examiner—Elbert L. Roberts
Attorney, Agent, or Firm—Oldham, Oldham & Weber Co.

[57] ABSTRACT

Tin steroids and methods of using the same. The tin steroid compounds are prepared by the reaction of various organotin compounds with various steroids. Said compounds inhibit the growth of malignant tumors. They are also useful as insecticides, larvicides, bactericides and fungicides.

15 Claims, No Drawings

TIN STEROIDS AND THEIR USES

CROSS REFERENCE TO RELATED APPLICATION

This application is a continuation-in-part of our copending application, Ser. No. 518,073, filed July 28, 1983, now U.S. Pat. No. 4,541,956, issued Sept. 17, 1985.

TECHNICAL FIELD

The present invention relates to a composition of, and preparation of, tin steroids, and their use as antineoplastic agents, bacteriacides, fungicides and insecticides.

BACKGROUND ART

Heretofore, with regard to the treatment of malignant growths such as various types of cancer and the like, the general approach of the medical and pharmaceutical professions has been keyed to the discovery of the causitive agents. The general approach by the pharmaceutical and medical industry has been to determine the nature of such agents, study the mechanism involved, and then create a pharmaceutical material that will intervene that mechanism.

It has now been discovered that the thymus gland of mammals processes exogenous tin into several biochemical compounds of a steroidal nature. Such tin steroids function as a critical component of the immune system, being involved in surveillance, detection and destruction of cells inimical to the well being of the host. Synthetic tin steroids, a hitherto unknown class of compounds have been prepared and found to be biologically highly active against mammalian tumors and tumor cells, pathogenic bacteria, and fungi. Furthermore, it has been discovered that select tin steroids interfere in the life processes of insects of public health and agricultural importance, and will destroy said insects directly through toxic activity, or indirectly by preventing metamorphosis, and in some instances acting as antifeedants.

DISCLOSURE OF INVENTION

It is therefore an aspect of the present invention to produce tin steroids.

It is another aspect of the present invention to produce tin steroids, as above, through the reaction of an organotin compound and a steroid.

It is a further aspect of the present invention to produce tin steroids, as above, by a process which is generally straight-forward and in which generally no toxic or hazardous by-products or compounds are produced.

It is yet another aspect of the present invention to produce tin steroids, as above, for use as an antineoplastic agent.

It is yet another aspect of the present invention to produce tin steroids, as above, for use as bactericidal agents.

It is yet another aspect of the present invention to produce tin steroids, as above, for use as antifungal agents.

It is yet another aspect of the present invention to produce tin steroids, as above, for use in insecticides and larvicides.

It is yet another aspect of the present invention to produce tin steroids, as above, for use as insect antifeedants.

It is yet another aspect of the present invention to produce tin steroids, as above, for use as juvenile hormone mimics.

It is yet another aspect of the present invention to produce tin steroids, as above, which can be orally administered.

It is yet another aspect of the present invention to produce tin steroids, as above, which have therapeutic value against malignant cells.

It is yet another aspect of the present invention to produce tin steroids, as above, which have prophylactic value against malignant cells.

It is yet another aspect of the present invention, to produce tin steroids, as above, that can be used to prevent or control infectious disease arising from pathogenic bacteria.

It is yet another aspect of the present invention to produce tin steroids, as above, that can be used to control monocellular plant growth.

It is yet another aspect of the present invention to produce tin steroids, as above, that can be used to control pathogenic and non-pathogenic fungi.

It is yet another aspect of the present invention to produce tin steroids, as above, that will control economic insects of public health and agricultural importance by direct toxic action.

It is yet another aspect of the present invention to produce tin steroids, as above, that will control certain economic insects by prevention of metamorphosis or prolongation of the larval period.

It is yet another aspect of the present invention to produce tin steroids, as above, that upon application to agricultural crops or stored food products will prevent insect damage by prevention of feeding activities.

These and other aspects of the present invention will become more apparent from the following detailed disclosure of the invention.

In general, a tin steroid compound comprises the reaction product of an organotin compound and a steroid.

In general, an antineoplastic process comprises the steps of administering an organotin steroid to an animal, said tin steroid being therapeutic towards malignant tumors and malignant cells.

In general, a bactericidal process is a process in which the tin steroid is impregnated in fabrics for hospital use, and upon contact with bacteria, serve to destroy such organisms or prevent their growth and proliferation.

In general, a fungicidal process is a process in which the tin steroid is impregnated in fabrics for hospital use, and upon contact with pathogenic fungi will prevent their growth and proliferation.

In general, an insecticidal process is a process in which the tin steroid is added to a water course in order to exert an insecticidal action against the aquatic larva of insects of public health importance, especially disease vectors.

In general, an insecticidal process is as process in which the tin steroid is applied to the soil in order to destroy insects that consume or damage agricultural plants.

In general, an antifeedant process is a process in which the tin steroid is applied directly to the growing plant and acts to prevent insect feeding thereon.

BEST MODE FOR CARRYING OUT THE INVENTION

The tin steroids of the present invention are produced by the reaction of an organotin compound with a steroid. Steroids have as a common nucleus, a fused-reduced 17 carbon atom ring system, cyclopentanoperhydrophenanthrene. The links of the side chains will vary and generally contain from 8 to 10 carbon atoms in the sterols, 5 carbon atoms in the bile acids, 2 carbon atoms in the adrenal cortical steroids, and none in the estrogens and androgens. Typically, the steroid utilized in the present invention has the following formulae:

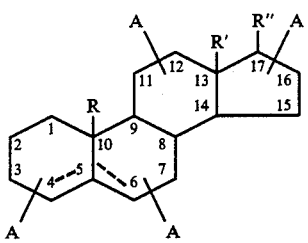

wherein R is hydrogen, or from 1 to 4 carbon atoms with either hydrogen or methyl being preferred. Similarly, R' is hydrogen or from 1 to 4 carbon atoms with hydrogen or methyl being preferred. R" can be hydrogen, oxygen, or from 1 to 12 carbon atoms, desirably, hydrogen, oxygen, or from 1 to 10 carbon atoms, with from 3 to 6 carbon atoms being preferred. The A group is either hydrogen or an alchol, that is an OH group, and is usually located at the 3, 7, 12 or 17 position. The dotted lines between positions 4 and 5 and between positions 5 and 6 denote optional double bonds. Preferred steroids include cholic acid, deoxycholic acid, testosterone, cholesteryl chloride, dehydroisoandrosterone, estrone, dexamethasone, adrenosterone, betamethason, cholanic acid, cholesterol, and corticosterone.

The organotin compounds are represented by the formulae:

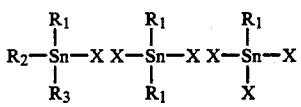

wherein $R_1$, $R_2$, and $R_3$ can be the same or different. $R_1$, $R_2$, and $R_3$ can be hydrogen or an alkyl group having from 1 to 6 carbon atoms, desirably from 3 to 5 carbon atoms, with 4 carbon atoms being preferred, an aromatic or an alkyl substituted aromatic having from 6 to 12 carbon atoms, such as a phenyl group, an aromatic substituted alkyl, for example a phenyl substituted alkyl wherein the alkyl group has from 7 to 12 carbon atoms, desirably from 9 to 11 and preferably 10 carbon atoms. X can be a hydroxy group, a halide, with chlorine being preferred, or a dicarboxylic acid group having from 2 to 10 carbon atoms with from 3 to 6 carbon atoms being preferred, such as adipic acid, succinic acid, or glutaric acid, a hydroxide oxide wherein $R_2$ and $R_3$ do not exist, or a monocarboxylic acid having from 2 to 6 carbon atoms, preferably 2 or 3 carbon atoms such as acetic acid. When X is a dicarboxylic acid, the acid will generally have the Sn, $R_1$, $R_2$, $R_3$ group extending off of both acid groups. Examples of preferred tin compounds include triphenyltin hydroxide, n-butyltin hydroxide oxide, triphenyltin chloride, tri-n-butyltin adipate, tri-n-butyltin chloride, hexamethylditin, n-propyltin trihalide, tri-n-butyltin fluoride, triethyltin halide, diethyltin halide, n-butyltin hydroxide oxide, trimethyltin halide, and triethyltin halide, with the first five-named compounds being preferred.

The tin steroids of the present invention are prepared by adding and dissolving the tin compound as well as the steroid in a mutually compatible solvent and heating. The solvent naturally is common to both compounds and also is inert thereto. Generally, a variety of solvents can be utilized such as alcohols having from 1 to 6 carbom atoms, preferably from 1 to 3 carbon atoms. Preferred compounds include chloroform, methanol, ethanol, and the like. The temperature to which the solution is heated is generally limited by the boiling point of the solvent. Generally, the reaction is carried out at a temperature of from about 60° to about 100° C., with from about 75° to about 85° C. being preferred. One particular manner of carrying out the reaction is to reflux the solution for a period of time, for example, a couple or ten hours. The reaction product can then be filtered and evaporated to remove most of the solvent and then cooled to beneath the melting point of the product to obtain the product. The molecular weight range of the organotin steroid compound generally is from about 400 to about 1,200, with from about 400 to about 800 being preferred.

The present invention is a clean system in that no foreign ingredients are utilized and thus a relatively pure product is produced. Moreover, the product has no toxicants, harmful by-products or other undesirable components therein in that the reaction generally yields either water or hydrochloric acid which can readily be removed.

The tin steroid compounds of the present invention can be utilized as antineoplastic inasmuch as they have tumor suppressing properties. Moreover, some of the compounds have even been found to kill malignant tumors. Also such compounds have been found to inhibit the proliferation of solid tumor cells and leukemic tumor cells. As such, the tin steroid compounds of the present invention have therapeutic value as well as prophylactic value. They also are non-toxic and a non-irritant with regard to the test animal.

Various tin steroids, according to the present invention were tested against mouse adenocarcinoma. Various tin steroids were also tested against mouse leukemia cells and human epidermoid tumor cells. Also, such compounds were tested against pathogenic bacteria, fungus, aquatic insect larva and adult insects. To better illustrate the nature and application of these compounds, a number of examples are given.

EXAMPLE 1

Triphenyltin hydroxide, in an amount of 3.67 g, was dissolved in 100 ml of ethanol, and 4.265 g of cholic acid were dissolved in 100 ml of ethanol. Both solutions were mixed in a 250 ml round bottomed flask with a soxhlet and a reflux condenser, and heated to boiling. The mixture was refluxed for two hours at 78° to 80° C. The reaction product was filtered and evaporated to one-fourth of its volume ~50 ml, then refrigerated at 6° C. to get crystals of the products.

Appearance: White flaky solid
Melting Point: 123°–127° C.

Molecular Weight (determined by mass spectrometer) = 720

Structure:

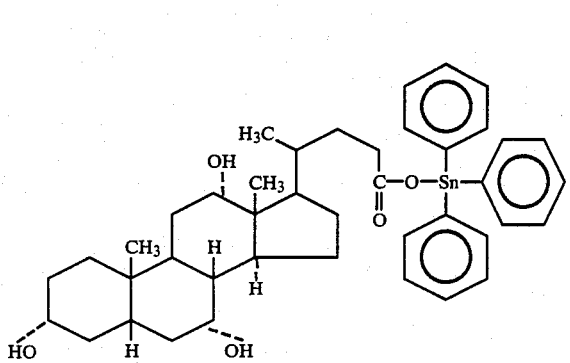

Triphenyltin cholate was evaluated against transplanted tumor fragments (mammary adenocarcinoma) in AK/I strain cancer prone mice at 10 ppm and 100 ppm administered continuously and ad libitum in drinking water. Results are shown in Table I and Table IV. Twenty mice were used, 10 male and 10 female, in each cohort; with three cohorts -0 ppm(control), 10 ppm and 100 ppm dosage regimen. Thirty days post transplant mice were sacrificed, the tumor and the tissues were extirpated and weighed. External tumor size measurements were made during the course of the experiment.

TABLE I
TRIPHENYLTIN CHOLATE EFFECT ON TUMOR GROWTH

| Cohort Factor | No. Mice | Agent Regimen | Average Tumor Wt. | No. Tumors | % Tumor as a Part of body wt. | Growth Suppression |
|---|---|---|---|---|---|---|
| 1 | 20 | 100 ppm | 0.1917 g | 20 | 1.35% | 6.26 |
| 2 | 20 | 10 ppm | 1.4281 g | 31 | 6.26% | 0.84 |
| 3 | 20 | 0 ppm | 1.2005 g | 32 | 4.95% | 1.00 |

The suppression effect is seen to be dose dependent.
At necropsy, organs were examined for signs of intoxication.
Liver, spleen, thymus and gastrointestinal tract were normal.
No gross effects of intoxication were present.
Weight gain was normal over the course of the experiment.

*Measured as
Tumor weight of controls mice
Tumor weight of test mice

EXAMPLE 2

CHOLESTERYL-n-BUTYL STANNATE 2.07 g of n-butyltin hydroxide oxide were dissolved in 90 ml of chloroform (partially dissolved in the cold); 3.86 g of cholesterol was dissolved in 90 ml of chloroform. The solutions were mixed in a 200 ml round bottomed flask fitted with a soxhlet and a reflux condenser and heated to boiling. The mixture was refluxed for three hours at 61° to 63° C. The reaction product in solution was filtered and evaporated to about 40 ml, then cooled at 6° C.

Appearance: White powder
Melting Point: 135°–141° C.
Calculated M.W.: 557
M.W. by spectroscopy: 520

Structure

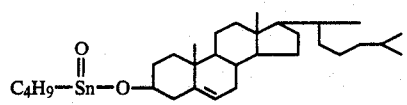

Mice provided with this material at 10 ppm and 100 pm over a six week period showed no signs of intoxication before sacrifice or at necropsy. Results are shown in Table IV.

EXAMPLE 3

TRIPHENYLTIN TESTOSTERONYL ETHER 3.5 g of triphenyltin chloride was dissolved in 40 ml of ethanol and 2.8 g of testosterone was dissolved in 40 ml of ethanol. Both solutions were mixed in a 200 ml round bottom flask fitted with a soxhlet and a reflux condenser. The mixture was refluxed for 3 hours at 78°–80° C. The reaction product duct was filtered and evaporated to ¼ its volume, then cooled to form a powder.

Appearance: amorphous powder
Melting point: 75°–80° C.
MW (determined by mass spec): 720

Structure

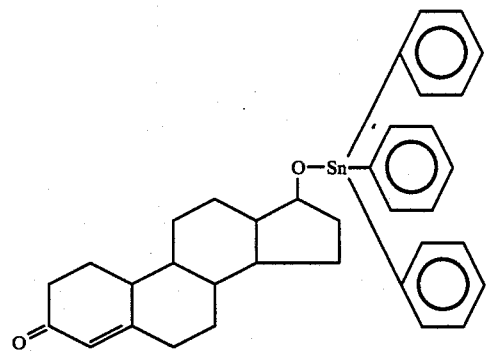

This compound was administered to mice in a manner similar to that described in Example 1. No toxic symptoms were evident prior to sacrifice nor upon examination of major organ systems at necropsy. Effects on tumor development are shown in Tables II and IV.

TABLE II
TRIPHENYLTIN TESTOSTERONYLETHER EFFECT ON TUMOR GROWTH

| Cohort | No. Mice | Agent Regimen | Average Tumor Wt. | No. Tumors | % Tumor as a Part of body wt. | Growth Suppression Factor |
|---|---|---|---|---|---|---|
| 1 | 20 | 100 ppm | 0.573 g | 19 | 2.00% | 2.1 |
| 2 | 20 | 10 ppm | 0.541 g | 25 | 1.89% | 2.2 |
| 3 | 20 | 0 ppm | 1.2005 g | 32 | 4.95% | 1.00 |

In one case of 20, the tumor transplant was destroyed by the agent. During the 30 day observation period, and upon necropsy, no toxicolgical alterations were evident.

EXAMPLE 4

TRIBUTYLTIN DEOXYCHOLATE 7.04 g of tributyltin adipate was partially dissoved in 40 ml of ethanol and 3.98 g of deoxycholic acid was dissolved in 40 ml of ethanol. Both solutions were mixed in a 200 ml round bottomed flask fitted with a soxhlet and a reflux condenser, and heated to boiling. The mixture was refluxed for three hours at 78° to 80° C. The reaction product was filtered and evaporated to one-fourth of its volume 20 ml, then cooled to form the product.

Appearance: White crystalline solid
Melting Point: 100°–104° C.
Molecular Weight: 682.5

Structure

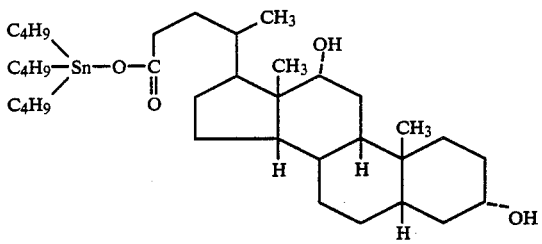

This primitive monoclinic crystal has the following cell parameters:

| a = 9.996 A° | 2 = 90.454° |
|---|---|
| b = 10.344 A° | B = 94.214° |
| c = 17.886 A° | r = 90.780° |
| Volume 1844.084 A°3 | |

This material was examined against transplanted tumors in AK/I mice with the effect noted in Tables III and IV.

TABLE III

TRIBUTYLTIN DEOXYCHOLATE
EFFECT ON TUMOR GROWTH

| Cohort | No. Mice | Agent Regimen | Average Tumor Wt. | No. Tumors | % Tumor as a Part of body wt. | Growth Suppression Factor |
|---|---|---|---|---|---|---|
| 1 | 20 | 100 ppm | 0.64 g | 23 | 3.85% | 1.88 |
| 2 | 20 | 10 ppm | 0.75 g | 24 | 2.86% | 1.60 |
| 3 | 20 | 0 ppm | 1.2005 g | 32 | 4.95% | 1.00 |

In cohort 1, five mice of the 20 subjects were completely free of tumors, i.e., agent destroyed 25 percent of the implanted tumors. No toxic symptoms were observed during the observation period or after necropsy. Weight gain was normal in all cases, and liver, spleen, thymus and G.I. tract showed no pathological alterations.

As apparent from Examples 1 through 4, the organotin compounds of the present invention are at least effective as a tumor growth suppressant and, in one case, even completely killed the cancerous growth.

Examples 5 through 20 relate to preparation of other tin steroid compounds of the present invention. Results of evaluation against mouse adenocarcinoma are shown in Table IV.

EXAMPLE 5

TRIPHENYLTIN CHOLESTERYL ETHER 3.67 g of triphenyltin hydroxide was dissolved in 80 ml of ethanol and 3.86 g of cholesterol was dissolved in 80 ml of ethanol. Both solutions were mixed in a 200 ml round bottom flask fitted with a soxhlet and reflux condenser, and heated to boiling. The mixture was refluxed for three hours at 78° to 80° C. The reaction product was filtered giving two fractions—a solid residue, dried at room temperature and a second material isolated by evaporation of the filtrate. Physical properties of the ethanol soluble species are:

| | Ethanol Soluble |
|---|---|
| Appearance: | white solid |
| Molec. weight | 736 |
| Melting point | 119–121° C. |

Structure

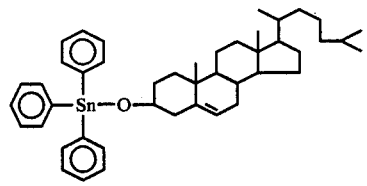

EXAMPLE 6

CHOLYL-n-BUTYL STANNATE 2.07 g of n-butyltin hydroxide oxide and 4.265 g of cholic acid were dissolved in 80 ml of ethanol. The mixture was refluxed for 20 hours at 78°–80° C. in a round bottomed flask fitted with a soxhlet and a reflux condenser. The reaction product was filtered and evaporated to one-fourth its volume, then cooled in a refrigerator to form crystals.

Appearance: White crystalline solid
Melting Point: 205°–218° C.
Calculated M.W.: 571.5

Structure

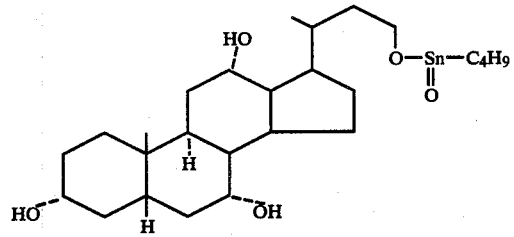

EXAMPLE 7

CHOLESTERYL TRIBUTYLTIN ETHER 7.04 g of tributyltin adipate and 4.05 g of cholesteryl chloride were dissolved in 80 ml of ethanol in a 200 ml round bottomed flask fitted with a soxhlet and a reflux condenser. The solution was refluxed at 78°–80° C. for eight hours. The reaction product was filtered, giving two fractions. The filtrate was evaporated to 10 ml and cooled in a refrigerator to form crystals.

Appearance: partially crystalline off-white powder
Melting Point: 83°–85° C.
Calculated M.W.: 959

Structure

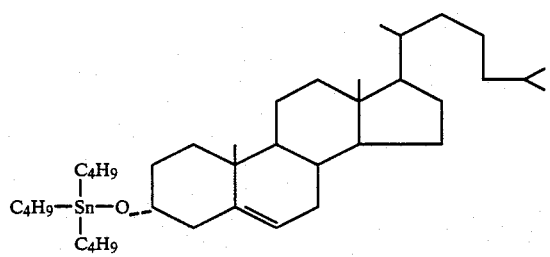

EXAMPLE 8

CHOLESTERYL TRIBUTYLTIN ADIPATE (FRACTION-2)

7.04 g of tributyltin adipate and 2.87 g of cholesterol were dissolved in 80 ml of ethanol in a 200 ml round bottomed flask fitted with a soxhlet and a reflux condenser. The solution was refluxed for eight hours at 78°–80° C. The filtrate was evaporated to one-fourth its volume and then cooled in a refrigerator. The residue was dried at room temperature. Two fractions were separated, using ethanol.

|  | 2. Filtrate (ethanol soluble) | 1. Residue (ethanol insoluble) |
| --- | --- | --- |
| Appearance | white crystalline flakes | white crystalline powder |
| Melting Point | 96–98° C. | 91–93° C. |
| Molecular wt. | 666 | 915 |

Fraction 1 was identified as dicholesteryl adipate (not a tin steroid).

Structure of Fraction 2

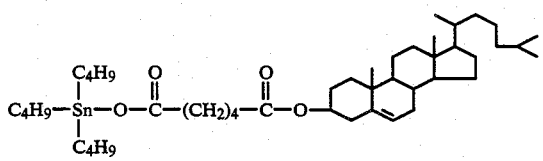

EXAMPLE 9

TRI-n-BUTYLTIN CHOLATE 3.25 g of tri-n-butyltin chloride and 4.08 g of cholic acid were dissolved in 80 ml of ethanol in a 200 ml round bottom flask fitted with a soxhlet and a reflux condenser. The solution was refluxed for 8 hours at 78°–80° C. The reaction product was filtered (residue was discarded), evaporated to about 10 ml, and cooled by refrigeration at 6° C.

Appearance: white amorphous solid
Melting Point: 89°–91° C.
Calculated MW: 715.0

Structure

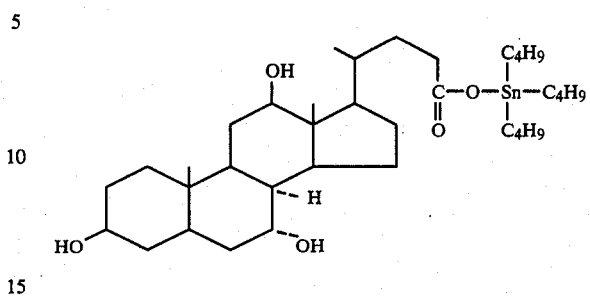

EXAMPLE 10

TESTOSTERONYL-n-BUTYL STANNATE 2.07 g of n-butyltin hydroxide oxide and 2.88 g of testosterone were dissolved in 80 ml of ethanol in a 200 ml round bottom flask fitted with a soxhlet and a reflux condenser. The solution was refluxed at 78°–80° C. for three hours. The reaction product was filtered and evaporated to dryness. The solid was recrystallized in ethanol.

Appearance: yellow crystals
Melting Point: 90°–95° C.
Calculated MW: 477.43

Structure

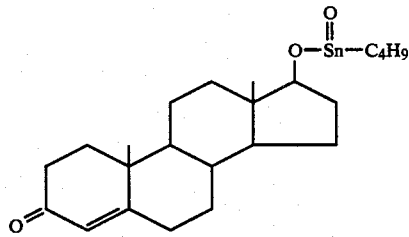

EXAMPLE 11

TRIPHENYLTIN TESTOSTERONYL ETHER 3.67 g of triphenyltin hydroxide and 2.88 g of testosterone were dissolved in 80 ml of ethanol in a 200 ml round bottom flask fitted with a soxhlet and a reflux condenser. The solution was refluxed at 78°–80° C. or three hours. The reaction product was filtered and evaporated to dryness. The solid was recrystallized in ethanol.

Appearance: yellow amorphous solid
Melting Point: 95°–98° C.
Calculated MW: 620.

Structure

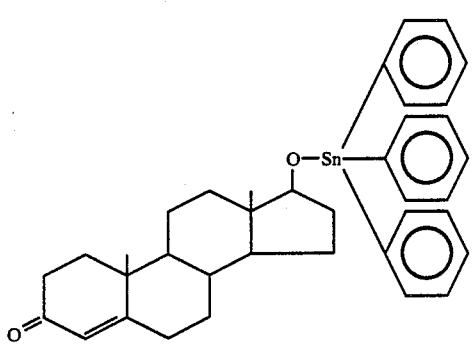

EXAMPLE 12
TRIPHENYLTIN DEHYDROISOANDROSTERONYL METHYLENEDI-p-PHENYLDIAMINE 2.47 g of dehydroisoandrosterone, 3.67 g of triphenyltin hydroxide, and 2.50 g methylenedi-p-phenyl diisocyanate were dissolved in 80 ml of ethanol in a 200 ml round bottom flask fitted with a soxhlet and a reflux condenser. The solution was refluxed at 78°–80° C. for three hours. The reaction product was filtered and evaporated to dryness. The solid was recrystallized in ethanol.

Appearance: yellow amorphous solid
Melting Point: 90°–95° C.
Calculated MW: 879

Structure

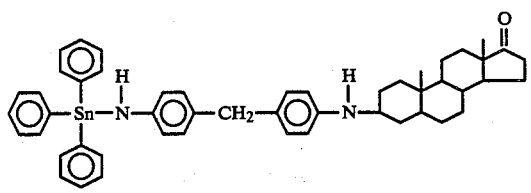

EXAMPLE 13
ESTRONYL-n-BUTYL STANNATE 2.07 g of n-butyltin hydroxide oxide and 2.70 g of estrone were combined in 80 ml of ethanol in 200 ml round bottom flask fitted with a soxhlet and a reflux condenser. The solution was refluxed for three hours at 78°–80° C. The reaction product was filtered and evaporated to dryness. The solid was recrystallized in ethanol.

Appearance: partially crystalline yellow solid
Melting Point: 205°–208° C.
Calculated MW: 459.36

Structure

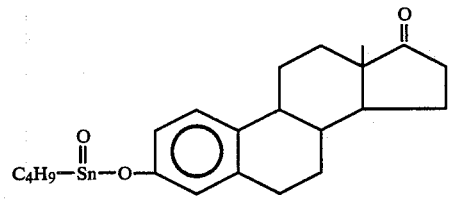

EXAMPLE 14
TRIMETHYLTIN CHOLATE 1.636 g of hexamethylditin and 4.085 g of cholic acid were dissolved in 80 ml of ethanol in a 200 ml round bottom flask fitted with a soxhlet and a reflux condenser. The solution was refluxed for two hours at 78°–80° C. The reaction product was filtered, evaporated to dryness, and recrystallized in ethanol.

Appearance: partially crystalline white solid
Melting Point: 90° C.–92° C.
Calculated MW: 571

Structure

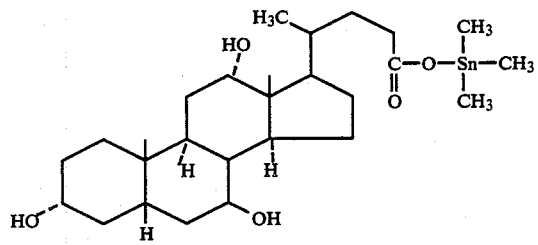

EXAMPLE 15
CORTICOSTERONYL-n-BUTYL STANNATE

Structure

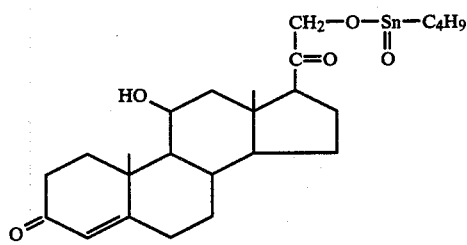

3.4645 g of corticosterone were dissolved in 80 ml of alcohol by heating 2.07 g of n-butyltin hydroxide oxide were dissolved in 80 ml of ethanol by heating. The two hot solutions were mixed in a 200 ml round bottom flask and a few drops of concentrated sulfuric acid were cautiously added to the mixture. The mixture was refluxed under nitrogen atmosphere for two hours at 78°–80° C. The mixture was then filtered and the filtrate was allowed to evaporate to dryness at room temperature. The solid product was redissolved in ethanol and recrystallized.

Appearance: Pale yellow crystals
Melting Point: 261°–262° C.
Molecular Weight: (theoretical) 535

EXAMPLE 16

DEOXYCORTICOSTERONYL-n-BUTYL STANNATE

Structure

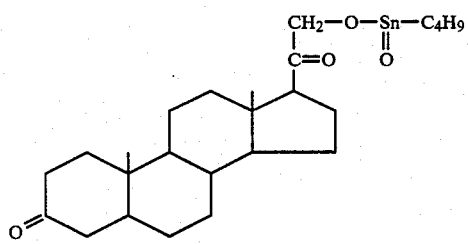

3.3045 g of deoxycorticosterone and 2.07 g of n-butyl tin hydroxide oxide were dissolved in 160 ml of hot alcohol. A little chromic oxide, $Cr_2O_3$ was added to the mixture which was refluxed under nitrogen atmosphere for two hours. The product was allowed to evaporate slowly under normal conditions. The solid was washed using 20 ml portions of water. Recrystallization was done using dioxane.
Appearance: Flaky
Melting Point: 200° C.–201° C.
Molecular Weight: 519

EXAMPLE 17

CORTISONYL-n-BUTYL STANNATE

Structure

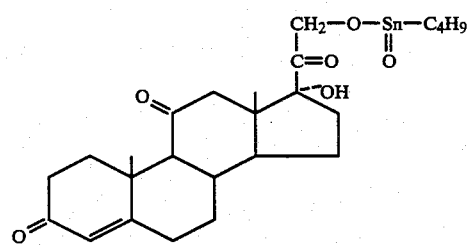

3.6046 g of cortisone and 2.07 g of n-butyltin hydroxide oxide were dissolved in 160 ml of 95% ethanol and a few drops of concentrated sulfuric acid were cautiously added to the mixture. The mixture was heated under reduced pressure for two hours. The product was slowly evaporated at room temperature. The solid was recrystallized from ethanol.
Appearance: Pale green platelets
Melting point: 195° C.
Molecular Weight: 549

EXAMPLE 18

DICHOLESTERYL-di-n-BUTYLTIN ETHER

Structure

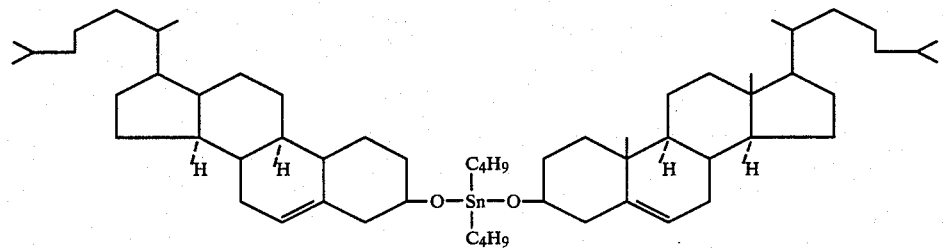

7.73 g of cholesterol and 3.04 g of dibutyltin dichloride was shaken with 160 ml of Pyridine and heated under reduced pressure for two hours. The reaction mixture was then filtered. The filtrate was agitated with 100 ml of water and filtered. The solid residue was washed with 20 ml portions of water, then recrystallized from ethanol.
Appearance: white powder
Melting Point: 149°–150° C.
Molecular Weight: 933

EXAMPLE 19

TRI-n-BUTYLTIN-BETA METHASONYL ETHER 3.9245 g of betamethasone and 3.2549 g of tri-n-butyltin chloride were dispersed in 160 ml of Pyridine and the mixture heated under reduced pressure for two hours. The reaction mixture was filtered. The filtrate was shaken with 100 ml of water and filtered. The solid residue was washed with 20 ml portion of water and recrystallized from ethyl acetate solution.
Appearance: Pale yellow powder
Melting Point: 219° C.
Molecular Weight: 644

Structure

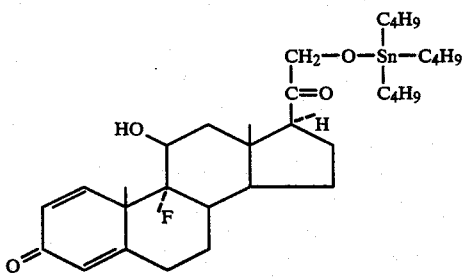

EXAMPLE 20

BETAMETHASONYL-n-BUTYL STANNATE

Structure

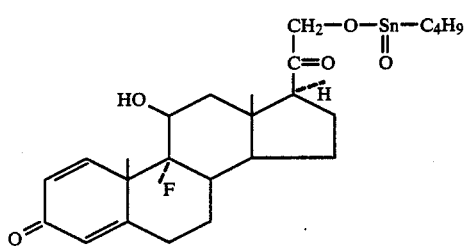

3.9245 g of betamethasone and 2.07 g of n-butyltin hydroxide oxide were dissolved in 180 ml of alcohol previously dried using anhydrous calcium chloride. A few drops of concentrated sulfuric acid were added to the mixture and refluxed at about 78° C. for two hours. The reaction product was allowed to stand on anhydrous potassium carbonate for 30 minutes; then filtered. The filtrate was evaporated to dryness at room temperature. The solid was recrystallized from ethyl acetate.

Appearance: Pale yellow powder
Melting Point: 197°
Molecular Weight: 581

Table IV presents the evaluation of certain tin steroids against mouse adenocarcinoma. The criterion used is the $(c/T) \times 100$ value wherein T represents the weight of the tumor in the test mouse and c represents the average weight of the tumors in the control mouse. A value in excess of 100 indicates that growth suppression occurred.

In some instances, the tumor fragment could not be located after diligent search or when located was totally necrotic. Since all such instances were observed with specific tin steroids and no such results were found with the control animals, it is believed that the tin steroid destroyed the fragment. All necrotic tumors lacked vascularization. Whether metastasis occurred in such circumstances is unknown. In cases where the fragment was missing or necrotic, no identifiable tumors were found in the G.I. Tract, liver, spleen, or kidney. Fat and muscle tissue were not examined, however.

Eighty control mice were used, in four cohorts of 20 subjects each. In all cases viable, large tumors were removed after sacrifice. Test mice were of the A/KI strain which is subject to adenocarcinoma and are considered to be cancer-prone.

TABLE IV
ADENOCARCINOMA SUPPRESSION IN A/KI MICE USING TIN SEROIDS

| Material | Dosage (ppm) | C/T × 100 | No. of Subjects |
|---|---|---|---|
| Triphenyltin cholate | 10 | 55 | 20 |
|  | 100 | 354 | 20 |
| Cholesteryl-n-butylstannate | 10 | 86 | 16 |
| Tryphenyltin testosterone | 10 | 255 | 10 |
|  | 100 | 237 | 10 |
| Tributyltin deoxycholate | 10 | 266 (2)* | 10 |
|  | 100 | 1352 (11)* | 21 |
| Triphenyltin cholesterol ether | 10 | 723 (3)* | 10 |
|  | 100 | 2350 (5)* | 15 |
| Cholesteryl tributyltin ether | 10 | 1707 (4)* | 12 |
|  | 100 | 2821 (6)* | 10 |
| Cholesteryl-tributyltin adipate | 10 | 182 | 10 |

TABLE IV-continued
ADENOCARCINOMA SUPPRESSION IN A/KI MICE USING TIN SEROIDS

| Material | Dosage (ppm) | C/T × 100 | No. of Subjects |
|---|---|---|---|
| (Fraction 2) | 100 | 2611 (2)* | 10 |

*The figure in parentheses refers to the number of mice wherein the tumor fragement could not be located or when found was totally necrotic.

In order to verify the tumor suppressive value of the tin steroids, materials were evaluated in tissue cell culture of the said tin steroids against mouse P-388 leukemia and human KB epidermoid tumor. Results are depicted in Table V. The test procedure follows the protocols of the National Cancer Institute.

TABLE V
INHIBITION INDICES FOR SEVERAL TIN STEROIDS

| | $ED_{50}$ (mcg/ml) | |
|---|---|---|
| Compound | Human KB Tumor | Mouse P-388 Leukemia |
| Triphenyltin cholate | 0.22 | 0.18 |
| Cholesteryl-n-butylstannate | 29 | 25.5 |
| Triphenyltin testosterone | 0.2 | 0.004 |
| Tributyltin deoxycholate | 0.25 | 0.26 |
| Triphenyltin cholesterol ether | 0.24 | 0.4 |
| Cholesteryl tributyltin ether | 0.3 | 5.0 |
| Cholesteryl tributyltin adipate (Fraction 2) | 0.20 | 0.05 |

The inspected bactericidal and fungicidal properties of the tin steroids were evaluated. Since one of the potential prophylactic usages envisioned was an impregnant for hospital fabrics the following test procedure was used.

Minimum Inhibitory Concentrations were determined by observing the presence or absence of microbial growth in a series of test tubes containing various concentrations of the test compound in a liquid medium. Due to the insolubility of most tin steroids in water, an initial 1/100 dilution of the compounds was made in dimethylformamide (DMF). After the dilution in DMF, serial dilutions were made using either nutrient broth (bacteria) or Sabouraud dextrose broth (fungi). The tubes were then inoculated with 0.1 ml of a broth culture of bacteria or 0.1 ml of a fungal spore suspension. Appropriate positive and negative controls were included.

The inoculated bacterial tubes were incubated at 37° C. for 72 hours, the fungal tubes were incubated at 28° C. for 10 days. The results were recorded on the basis of visual microbial growth.

Results are shown in Table VI.

A solution of tri-n-butyltin deoxycholate (TBT-DOC) was padded on 3 different types of fabric:
(1) desized, scoured and bleached all cotton broadcloth
(2) 100% nylon
(3) 50:50/Cotton:Polyester After drying, the fabrics were laundered according to AATCC Method 61-1980 (IIA) and samples were taken after 0, 5, 10, 15 and 25 washes and tested according to AATCC Method 147-1982 and AATCC Method 30-1981. (AATCC is an abbreviation for American Association of Textile Chemists and Colorists)

The unwashed samples were analyzed for their tin content according to AATCC Method 94-1977-Appendix A1. The formulated TBT-DOC was added to 100% mercerized cotton socks during the softening cycle in a Milner machine with an add-on of 333 ppm active ingredient.

The socks were dried, boarded and tested as per the fabrics in the above section.

Results are shown in Tables VII and VIII.

TABLE VI

| Minimum Inhibitory Concentrations | S. aureus | K. pneumoniae | A. niger |
| --- | --- | --- | --- |
| Triphenyltin cholate | 2-6 ppm | 40 ppm | 2-6 ppm |
| Triphenyltin testosterone | 10-16 | 40 | 2 |
| Tri-n-butyltin deoxycholate | 1.25-2.5 | 30 | 10-15 |
| Triphenyltin cholesteryl ether | 40 | 40 | 20-26 |
| Cholesteryl tributyltin adipate | 6-10 | 40 | 20-26 |
| Tri-n-butyltin cholate | 10-16 | 40 | 26-32 |
| Testosteronyl-n-butylstannate | 40 | 40 | 40 |
| Triphenyltin testosteronyl ether | 2-6 | 40 | 10-16 |
| Trimethyltin cholate | 40 | 40 | 40 |
| Cholesteryl tri-n-butyltin maleate | 2.5-4 | 20-25 | 35-50 |

TABLE VII

| | Microbiological Tests on Impregnated Fabrics | | | | | | | | | | | |
| --- | --- | --- | --- | --- | --- | --- | --- | --- | --- | --- | --- | --- |
| No. of | Nylon | | | | Cotton | | | | Cotton:Poly | | | |
| Washes | S | K | A | C | S | K | A | C | S | K | A | C |
| 0 | 6 | 1 | 4 | 426 | 4 | 1 | 4 | 446 | 5 | 1 | 4 | 357 |
| 5 | 3 | 0 | 2 | — | 4 | 0 | 3 | — | 5 | 0 | 2 | — |
| 10 | 2 | 0 | 2 | — | 2 | 0 | 3 | — | 2 | 0 | 1 | — |
| 15 | 1 | 0 | 2 | — | 1 | 0 | 2 | — | 1 | 0 | 0 | — |
| 25 | 0 | F | 2 | — | 0 | 0 | 0 | — | F | F | F | — |

TABLE VIII

| Microbiological Tests, Plant Trial | | | |
| --- | --- | --- | --- |
| No. of Washes | S | K | A |
| 0 | 7 | 0 | 10 |
| 5 | 5 | 0 | 10 |
| 10 | 3 | 0 | 10 |
| 15 | 2 | 0 | 9 |
| 25 | 1 | 0 | 7 |

Notes on Tables VII and VIII:
1 The numbers in the chart above are the sizes of clear zones (halos) around the fabric specimen where microbial growth was completely inhibited, as measured in millimeters.
2 0 = no halo but complete inhibition of microbial growth on contact with fabric.
3 F = no halo and no contact inhibition; i.e. complete failure of specimen to resist microbial growth
4 S = S. aureus
5 K = K. pneumoniae
6 A = A. niger
7 C = Chemical analysis - ppm TBT-DOC Insecticidal activity was evaluated on 2 to 5 day old adult larvae of *Musca domestica*, the common house fly, the adult *Sitophilus oryzae*, the rice weevil. Larvicidal activity was assessed for fifth instar larvae of *Spodoptera litura*, the tobacco caterpillar, the army worm *Mythimna separata*, and three species of mosquitoes (IV Instar); *Aedes aegypti*, yellow fever vector, *Anopheles stephensi*, malaria vector, and *Culex fatigans*, and filaria vector.

Compounds were topically applied to the house fly and tobacco caterpillar at different concentrations. The rice weevil was exposed to residual films of the test compound on glass surfaces for 24 hours. For the aquatic mosquito larvae, the test compounds were added at various concentrations to the water container. Results of the above tests are shown in Tables IX through XII.

TABLE IX

| | Insecticidal Activity at Various Dosages | | | | | |
| --- | --- | --- | --- | --- | --- | --- |
| | House Fly | | | Rice Weevil | | |
| Dosage | % Mortality | | | | | |
| Compound | 1.0 mcg* | 5.0 mcg | 10.0 mcg | 1.0 mcg | 5.0 mcg | 10.0 mcg |
| Triphenyltin cholesterol ether | 10 | 30 | 100 | NT** | NT | 0 |
| Tributyltin deoxycholate | 0 | 5 | 96.7 | NT | NT | 0 |
| Cholesteryl tributyltin ether | 0 | 20 | 100 | NT | NT | 0 |
| Cholesteryl tributyltin adipate (Fraction 2) | 0 | 20 | 100 | NT | NT | 0 |
| Triphenyltin testosteronyl ether | 0 | 0 | 75 | NT | NT | 0 |
| Triphenyltin dehydroisoandrosterone | 5 | 40 | 100 | NT | NT | 0 |
| Trimethyltin cholate | 0 | 100 | 100 | 95 | 100 | 100 |

*mcg = micrograms per insect, topical application
**NT = not tested

TABLE X

| | Tin Steroid Activity Against Aquatic Larva | | | | | | | | |
| --- | --- | --- | --- | --- | --- | --- | --- | --- | --- |
| | (% Mortality at 24 hours) | | | | | | | | |
| Dosage (ppm) | A. aegypti | | | C. fatigans | | | A. stephonsi | | |
| Compound | 1 | 5 | 10 | 1 | 5 | 10 | 1 | 5 | 10 |
| Triphenyltin cholate | 70 | 76.7 | 100 | 46.7 | 100 | 100 | NT | 100 | 100 |
| Triphenyltin testosterone | 60 | 100 | 100 | 0 | 100 | 100 | NT | 100 | 100 |
| Tributyltin deoxycholate | NT | NT | 93 | 66 | 100 | 100 | NT | NT | 96.7 |

TABLE X-continued

| | Tin Steroid Activity Against Aquatic Larva | | | | | | | | |
|---|---|---|---|---|---|---|---|---|---|
| | (% Mortality at 24 hours) | | | | | | | | |
| Dosage (ppm) | A. aegypti | | | C. fatigans | | | A. stephonsi | | |
| Compound | 1 | 5 | 10 | 1 | 5 | 10 | 1 | 5 | 10 |
| Triphenyltin cholesterol ether | 36.7 | 100 | 100 | 93 | 100 | 100 | NT | 100 | 100 |
| Cholesteryl tributyltin ether | 0 | 80 | 100 | NT | 100 | 100 | NT | 100 | 100 |
| Cholesteryl tributyltin adipate (Fraction 2) | 10 | 100 | 100 | 10 | 100 | 100 | NT | 100 | 100 |
| Tributyltin cholate | 25 | 100 | 100 | 50 | 100 | 100 | NT | 100 | 100 |
| Triphenyltin testosteronyl ether | NT | NT | 93 | 80 | 100 | 100 | NT | 100 | 100 |
| Triphenyltin dehydroiso androsterone | 0 | 100 | 100 | 5 | 100 | 100 | NT | NT | 20 |
| Trimethyltin cholate | NT | NT | 63 | 0 | 73.3 | 100 | NT | NT | 23.3 |

TABLE XI

| | Tin Steroid Activity Against Non-Aquatic Larva | | | | | |
|---|---|---|---|---|---|---|
| | (% Mortality in 24 Hours Exposure) | | | | | |
| | Caterpillar | | | Army Worm | | |
| | Dosage (mcg/Insect) | | | | | |
| Compound | 1 | 5 | 10 | 1 | 5 | 10 |
| Tributyltin deoxycholate | NT | NT | 30 | NT | NT | 0 |
| Cholesteryl tributyltin ether | NT | NT | 20 | NT | NT | 30 |
| Trimethyltin cholate | 20 | 100 | 100 | 65 | 100 | 100 |

The pulse beetle, *Callosobruchus maculatus* and the red cotton bug *Dysdercus keonigii* were also exposed to various dosages of tin steroids in a separate study. Results are shown in Table XII.

TABLE XII

| | Tin Steroid Activity Against Larva of The Pulse Beetle and Red Cotton Bug | | | |
|---|---|---|---|---|
| | Compound | | | |
| | Tributyltin deoxycholate | | Testosteronyl-n-butylstannate | |
| Dose (mcg/insect) | % Mortality | | | |
| | Pulse Beetle | Cotton Bug | Pulse Beetle | Cotton Bug |
| 1.0 | NT | NT | 100 | NT |
| 2.5 | NT | NT | 100 | 15 |
| 5.0 | NT | NT | 100 | 80 |
| 10.0 | 80 | 0 | 100 | 100 |

Antifeedant activity was evaluated against *M. domestica* adults and *S. litura*. Compounds were offered in 0.05M sucrose solution to *M. domestica*, and the same solution offered on castor leaves to *S. litura*. Exposure times were 24 and 48 hours. Results are shown in Table XIII.

TABLE XIII

| Antifeedant Activity Against Spodoptera litura | | |
|---|---|---|
| | % Protection at 0.1% | |
| Compound | 24 hrs. | 48 hrs. |
| Triphenyltin cholate | 75.99 | 80.93 |
| Cholesteryl-n-butyl-stannate | 9.4 | 2.9 |
| Triphenyltin testosterone | 100 | 100 |
| Tributyltin deoxycholate | 100 | 100 |
| Triphenyltin cholesterol ether | 94.99 | 95.98 |
| Cholesteryl tributyltin ether | 100 | 100 |
| Cholesteryl tributyltin adipate | 100 | 100 |
| Tributyltin cholate | 100 | 100 |
| Testosteronyl-n-butyl-stannate | 3.9 | 0 |
| Triphenyltin testosteronyl ether | 100 | 95.27 |
| Triphenyltin dehydro-isoandrosterone | 100 | 98.04 |
| Trimethyltin cholate | 96.84 | NT |

Juvenile hormone activity was measured on the red cotton bug. Compounds were applied to freshly emerged fifth instar nymphs kept on water and metamorphosis inhibition was recorded at the time of larval adult molt. Results are shown in Table XIV.

TABLE XIV

| Juvenile hormone activity of some tin compounds against Sysdercus koenigii | |
|---|---|
| Compound | % Metamorphosis inhibition at 10 mcg per insect |
| Triphenyltin cholate | 0.66 |
| Cholesteryl-n-butyl-stannate | 0.6 |
| Tributyltin deoxycholate | 1.65 |
| Cholesteryl tributyltin ether | 7.1 |
| Cholesteryl tributyltin adipate (Fraction 2) | 15.8 |
| Tributyltin cholate | 7.25 |
| Testosteronyl-n-butyl-stannate | 0 |
| Triphenyltin dehydroisoandrosterone | 5.63 |
| Estronyl-n-butyl-stannate | 1.0 |

While in accordance with the patent statutes, the best mode and preferred embodiment has been described in detail, the invention is not to be limited thereby, the scope of the invention being limited solely by the scope of the attached claims.

What is claimed is:

1. A method for inhibiting the growth of tumor cells or for killing, microbes, insects and larve,
   which comprises administering a tin steroid compound, said tin steroid compound being the reaction product of a steroid compound and a tin compound,
   wherein the steroid compound is selected from the group consisting of cholic acid, testosterone, deoxycholic acid, cholesteryl chloride, cholesterol, dehydroxycholesterol, dehydroisoandrosterone, and estrone and said tin compound has one of the formulae:

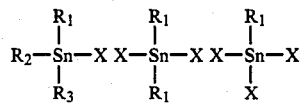

wherein $R_1$, $R_2$, and $R_3$ can be the same or different, wherein said $R_1$, $R_2$ and $R_3$ are selected from the group consisting of hydrogen, an alkyl having from 1 to 6 carbon atoms, a cycloalkyl having from 4 to 10 carbon atoms, an aromatic or an alkyl substituted aromatic having from 6 to 12 carbon atoms, and an aromatic substituted alkyl having from 7 to 12 carbon atoms, and where X is selected from the group consisting of hydroxyl, halide, hydroxide oxide wherein $R_2$ and $R_3$ do not exist, a dicarboxylic acid having from 2 to 10 carbon atoms, and a moncarboxylic acid having from 2 to 6 carbon atoms.

2. A method according to claim 1 wherein said tin compound has the formula:

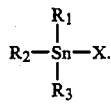

3. A method according to claim 1 wherein said organotin compound is selected from the group consisting of triphenyltin hydroxide, n-butyltin hydroxide oxide, triphenyltin chloride, hexamethylditin, n-propyltin trihalide, tri-n-butyltin fluoride, triethyltinhalide, diethyltin dihalide, di-n-butyltin dihalide, n-butyltin hydroxide oxide, trimethyltin halide, and triethyltin halide.

4. A method according to claim 1 including administering an amount of said tin steroid of from about 1.7 mcg to about 100 mcg daily, based upon each gram of body weight.

5. A method according to claim 1, wherein the tin steroid is administered to an animal to inhibit growth of tumor cells.

6. A method according to claim 5, wherein the animal is a warm blooded animal.

7. A method according to claim 6, wherein said warm blooded animal is a mammal.

8. A method according to claim 1, wherein the tin steroid is impregnated in cloth to destroy pathogenic bacteria and fungus.

9. A method according to claim 1, wherein the tin steroid is topically applied to mammals to protect against bacterial or fungal infections.

10. A method according to claim 1 wherein the tin steroid is applied to infested water to destroy mosquito larvae.

11. A method according to claim 10, wherein the tin steroid as added as a solution or emulsion to said water course to destroy mosquito larvae.

12. A method according to claim 10, wherein the tin steroid is added in solid form in a controlled release dispenser to destroy mosquito larvae.

13. A method according to claim 1, wherein the tin steroid is applied by spraying to agricultural crops, pastures, grasslands or domestic animals to destroy adult or larval insects.

14. A method according to claim 1, wherein the tin steroids are sprayed on growing crops to provide antifeedant action against pest insects.

15. A process for preparing a tin steroid, which comprises reacting a steroid compound with a tin compound,
wherein the steroid compound is selected from the group consisting of cholic acid, testosterone, dioxycholic acid, cholesteryl chloride, cholesterol, dhydroxycholesterol, dehydroisoandrosterone, and estrone and said tin compound has one of the formulae:

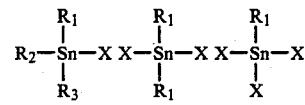

wherein $R_1$, $R_2$ and $R_3$ can be the same or different, wherein said $R_1$, $R_2$ and $R_3$ are selected from the group consisting of hydrogen, an alkyl having from 1 to 6 carbon atoms, a cycloalkyl having from 4 to 10 carbon atoms, an aromatic or an alkyl substituted aromatic having from 6 to 12 carbon atoms, and an aromatic substituted alkyl having from 7 to 12 carbon atoms, and where X is selected from the group consisting of hydroxyl, halide, hydroxide oxide wherein $R_2$ and $R_3$ do not exist, a dicarboxylic acid having from 2 to 10 carbon atoms, and a monocarboxylic acid having from 2 to 6 carbon atoms.

* * * * *